United States Patent
Davis

(10) Patent No.: US 10,828,487 B2
(45) Date of Patent: Nov. 10, 2020

(54) COCHLEAR IMPLANT ASSEMBLIES AND METHODS FOR MANUFACTURING THE SAME

(71) Applicant: Advanced Bionics AG, Staefa (CH)

(72) Inventor: Austin Charles Davis, North Hollywood, CA (US)

(73) Assignee: Advanced Bionics AG, Staefa (CH)

( * ) Notice: Subject to any disclaimer, the term of this patent is extended or adjusted under 35 U.S.C. 154(b) by 120 days.

(21) Appl. No.: 16/162,272

(22) Filed: Oct. 16, 2018

(65) Prior Publication Data

US 2020/0114144 A1    Apr. 16, 2020

(51) Int. Cl.
| | | |
|---|---|---|
| *A61N 1/05* | (2006.01) | |
| *A61N 1/375* | (2006.01) | |
| *A61N 1/36* | (2006.01) | |
| *A61N 1/37* | (2006.01) | |

(52) U.S. Cl.
CPC ....... *A61N 1/0541* (2013.01); *A61N 1/36038* (2017.08); *A61N 1/375* (2013.01); *A61N 1/3718* (2013.01); *A61N 1/3756* (2013.01)

(58) Field of Classification Search
CPC .. A61N 1/0541; A61N 1/36038; A61N 1/375; A61N 1/3756; A61N 1/3718
USPC ............................ 607/36, 136, 137, 116, 152
See application file for complete search history.

(56) References Cited

U.S. PATENT DOCUMENTS

| | | | |
|---|---|---|---|
| 8,594,799 B2 * | 11/2013 | Haller ................ | A61B 17/3468 607/57 |
| 9,782,584 B2 | 10/2017 | Cartledge et al. | |
| 9,919,154 B2 | 3/2018 | Lee et al. | |
| 2009/0299437 A1 * | 12/2009 | Zimmerling ....... | A61N 1/36036 607/57 |
| 2012/0130396 A1 * | 5/2012 | Tockman ............... | A61N 1/375 606/129 |
| 2017/0100597 A1 * | 4/2017 | Barror ................. | A61N 1/3758 |

FOREIGN PATENT DOCUMENTS

CN          101862228          4/2013

* cited by examiner

*Primary Examiner* — Carl H Layno
*Assistant Examiner* — Anh-Khoa N Dinh
(74) *Attorney, Agent, or Firm* — ALG Intellectual Property, LLC

(57) ABSTRACT

An exemplary cochlear implant assembly includes an implantable cochlear stimulator (ICS) configured to apply electrical stimulation to a recipient by way of an electrode array. The ICS is housed in a casing that comprises a first surface area configured to serve as a current path to ground for the electrical stimulation and a second surface area. The cochlear implant assembly further includes an encapsulant that includes a conductive portion configured to cover the first surface area of the casing and be in conductive contact with the first surface area such that the conductive portion serves as the ground electrode and a non-conductive portion configured to cover the second surface area of the casing such that the casing is entirely disposed within the conductive and non-conductive portions of the encapsulant. Corresponding methods for manufacturing cochlear implant assemblies are also described.

20 Claims, 9 Drawing Sheets

COCHLEAR IMPLANT ASSEMBLIES AND METHODS FOR MANUFACTURING THE SAME

BACKGROUND INFORMATION

Cochlear implant systems are used to provide, restore, and/or improve the sense of hearing to recipients with severe or profound hearing loss. Conventional cochlear implant systems include various components configured to be implanted within a recipient (e.g., a cochlear implant, an antenna, and an electrode lead) and various components configured to be located external to the recipient (e.g., a sound processor, a battery, and a microphone). Typically, at least some of the implanted components of a cochlear implant system are provided within an encapsulant formed of a biocompatible material such as medical grade silicone.

Unfortunately, after the components of a cochlear implant system are implanted within the recipient, biofilms can form on surfaces of the implanted components. For example, certain openings (e.g., a magnet pocket opening, a ground electrode opening, etc.) in the encapsulant are particularly susceptible to biofilm formation. Such biofilms provide ideal conditions for bacterial growth and survival, which can cause inflammation and persistent infections that may not heal while the components of the cochlear implant system are implanted within the recipient. Moreover, such biofilms can cause device failure. As such, the formation of biofilms causes distress to the recipient of the cochlear implant system and may undesirably require a surgery to remove and replace the implanted components.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Cochlear implant assemblies and methods for manufacturing the same are described herein. An exemplary cochlear implant assembly described herein includes an implantable cochlear stimulator (ICS) configured to apply electrical stimulation to the recipient by way of an electrode array. As will be described in more detail below, the ICS is housed within a casing that comprises a first surface area configured to provide a current path to ground for the electrical stimulation and a second surface area. The exemplary cochlear implant assembly further comprises an encapsulant that includes a conductive portion configured to cover at least a substantial portion of the first surface area of the casing and be in conductive contact with the first surface area such that the conductive portion serves as the ground electrode, and a non-conductive portion configured to cover at least a substantial portion of the second surface area of the casing such that the casing is entirely disposed within the conductive and non-conductive portions of the encapsulant.

The cochlear implant assemblies described herein may provide various benefits to cochlear implant recipients, as well as others involved with managing cochlear implant systems. For example, the cochlear implant assemblies described herein reduce the number of openings, voids, recesses, or other discontinuities provided in the encapsulant. As a result, the cochlear implant assemblies are less susceptible to biofilm formation, infection, and/or device failure than conventional cochlear implant assemblies. In addition, because such cochlear implant assemblies are less susceptible to infection, they are easier to manage by clinicians and provide less distress to recipients of cochlear implant systems. Accordingly, cochlear implant systems that use cochlear implant assemblies such as those described herein are more robust and potentially have a longer operational life than cochlear implant systems that use conventional cochlear implant assemblies.

Various embodiments will now be described in more detail with reference to the figures. The disclosed cochlear implant assemblies and methods may provide one or more of the benefits mentioned above and/or various additional and/or alternative benefits that will be made apparent herein.

Figure 1:
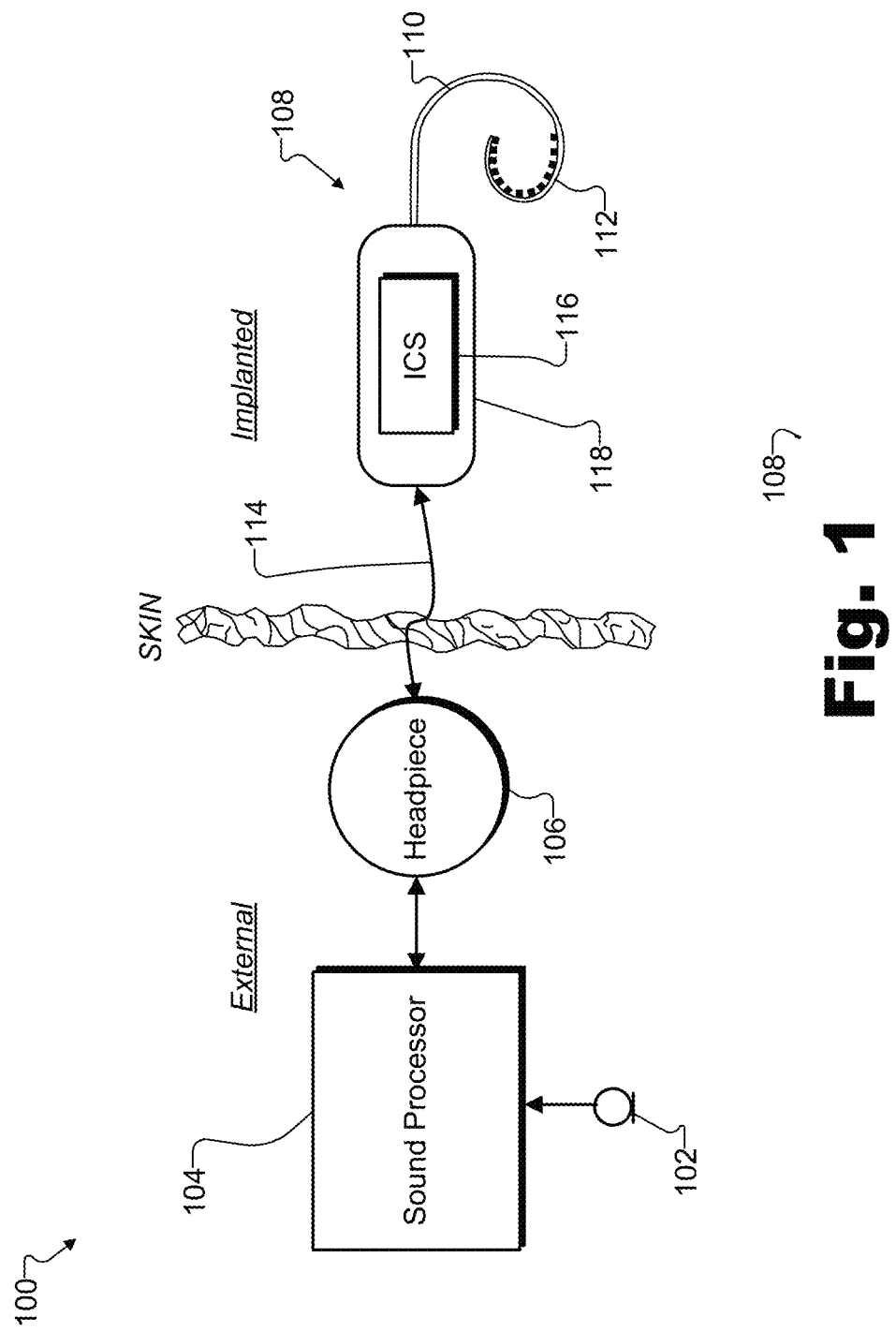
FIG. 1 illustrates an exemplary cochlear implant system according to principles described herein.

FIG. 1 illustrates an exemplary cochlear implant system 100. As shown, cochlear implant system 100 may include a microphone 102, a sound processor 104, a headpiece 106 having a coil disposed therein, and a cochlear implant 108 that includes an electrode lead 110 and an ICS 116 housed within a casing 118. Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown in FIG. 1) may also be disposed on other parts of electrode lead 110 (e.g., on a proximal portion of electrode lead 110) and/or elsewhere on cochlear implant 108 to, for example, provide a current return path for stimulation current generated by electrodes 112 and to remain external to the cochlea after electrode lead 110 is inserted into the cochlea. Additional or alternative components may be included within cochlear implant system 100 as may serve a particular implementation.

As shown, cochlear implant system 100 may include various components configured to be located external to a recipient including, but not limited to, microphone 102, sound processor 104, and headpiece 106. Cochlear implant system 100 may further include various components configured to be implanted within the recipient including, but not limited to, cochlear implant 108 including electrode lead 110, ICS 116, and casing 118. As will be described in more detail below, at least some of the components that are configured to be implanted within the recipient are encapsulated within an encapsulant (not shown in FIG. 1) that may be made of any suitable biocompatible material, such as medical grade silicone.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by ICS 116 that is housed within casing 118, as shown in FIG. 1. In some alternative implementations, cochlear implant 108 may include a brainstem implant and/or any other type of implantable stimulator that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the recipient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
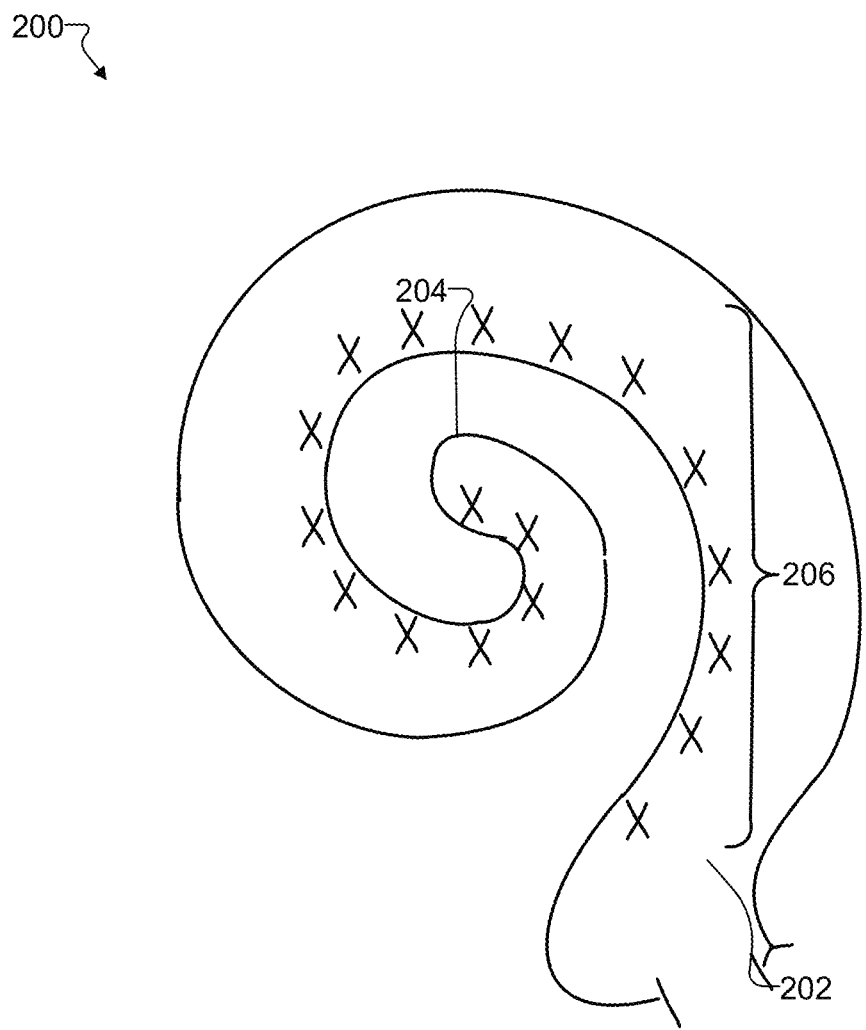
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the recipient perceiving relatively low frequencies and electrical stimulation applied by way of electrodes disposed within the basal region (i.e., "basal electrodes") may result in the recipient perceiving relatively high frequencies. The delineation between the apical and basal electrodes on a particular electrode lead may vary depending on the insertion depth of the electrode lead, the anatomy of the recipient's cochlea, and/or any other factor as may serve a particular implementation.

An encapsulant is provided as part of a cochlear implant to protect certain components of a cochlear implant system while such components are implanted within a recipient. For example, an encapsulant may encapsulate casing 118 of cochlear implant 108, an antenna configured to communicate with an external antenna included in headpiece 106, a magnet or magnet apparatus, and/or various other implantable components.

Encapsulants such as those described herein may be formed in any suitable manner as may serve a particular implementation. In certain examples, an encapsulant may be overmolded around certain components (e.g., casing 118, electrode lead 110, etc.) included in cochlear implant 108. Alternatively, an encapsulant may be formed through casting, spraying, dipping, or any other suitable manufacturing method.

In conventional cochlear implants, an encapsulant includes a void that exposes a conductive top surface of casing 118 of cochlear implant 108 that serves as a current path to ground for stimulation provided by cochlear implant 108 via electrodes 112. In this manner, the top surface of casing 118 of cochlear implant 108 may be conductively exposed while cochlear implant 108 is within the recipient. Unfortunately, the void included in the conventional encapsulant is an area where biofilm can potentially form. Hence, the cochlear implants described herein include encapsulants that have fewer voids/openings than conventional encapsulants.

For example, as will be described in more detail below, instead of having a void that exposes a surface of casing 118 of cochlear implant 108 that is configured to provide a path to ground, encapsulants such as those described herein include a conductive portion and a non-conductive portion that together entirely cover casing 118 of cochlear implant 108. The conductive portion is configured to serve as a ground electrode for the electrical stimulation by virtue of the conductive portion providing a current path to ground and being conductively isolated from other surfaces of casing 118 by the non-conductive portion.

The conductive portion of an encapsulant may be formed of any suitable biocompatible conductive material. For example, the conductive portion may be formed of a conductive elastomer or of silicone that is impregnated with conductive particles (e.g., carbon particles, platinum particles, and/or titanium particles) to render it conductive. The conductive portion of the encapsulant covers and is in conductive contact with a surface area of casing 118 of cochlear implant 108 that is configured to provide a current path to ground for electrical stimulation provided by cochlear implant 108. As such, the conductive portion serves as the ground electrode.

Any suitable surface area or combination of surface areas of casing 118 of cochlear implant 108 may be configured to serve as a current path to ground for electrical stimulation provided by cochlear implant 108. For example, a surface area of casing 118 of cochlear implant 108 that is configured to serve as a current path to ground may face away from the skull of the recipient after the cochlear implant assembly is implanted within the recipient. In examples where casing 118 of cochlear implant 108 includes a plurality of surface areas that are each configured to serve as a current path to ground, each surface area included in the plurality of surface areas may be provided on the same side of casing 118 of cochlear implant 108 (e.g., the side that faces away from the skull of the recipient). Alternatively, the surface areas may be provided on different sides (e.g., opposite sides) of casing 118 of cochlear implant 108 in certain implementations.

The conductive portion of an encapsulant as described herein may have any suitable size and may cover any suitable surface area or combination of surface areas of casing 118 of cochlear implant 108 that may be configured to serve as the current path to ground. For example, only one conductive portion may be provided so as to cover a single surface area of casing 118 of cochlear implant 108 that is configured to serve as the current path to ground. Alternatively, the conductive portion may include two or more conductive portions that are conductively isolated from each other and that each covers a respective surface area of casing 118 of cochlear implant 108 that is configured to serve as a current path to ground. Examples of conductive portions of an encapsulant are described herein.

The non-conductive portion of an encapsulant may be considered to be any portion of the encapsulant that does not include the conductive portion. In other words, the nonconductive portion is any portion that is not conductive and that does not cover the surface area of casing 118 of cochlear implant 108 configured to serve as the current path to ground. The non-conductive portion of an encapsulant may be formed of any suitable biocompatible insulative material. For example, the non-conductive portion of the encapsulant may be formed of medical grade silicone, polyurethane, a thermoplastic elastomer, and/or any other suitable material. The non-conductive portion of the encapsulant is configured to bond to an outer periphery of the conductive portion of the encapsulant during manufacture such that there is no void, opening, or other significant discontinuity on an exterior surface of the encapsulant that separates the conductive portion and the non-conductive portion where biofilm could form.

The encapsulant may have any suitable thickness from casing 118 as may serve a particular implementation. In certain examples, the thickness of the encapsulant may be between 0.25 millimeters to 0.5 millimeters from a surface of casing 118. Various exemplary cochlear implant assemblies that may be provided according to principles described herein will now be described with reference to FIGS. 3-8.

Figure 3:
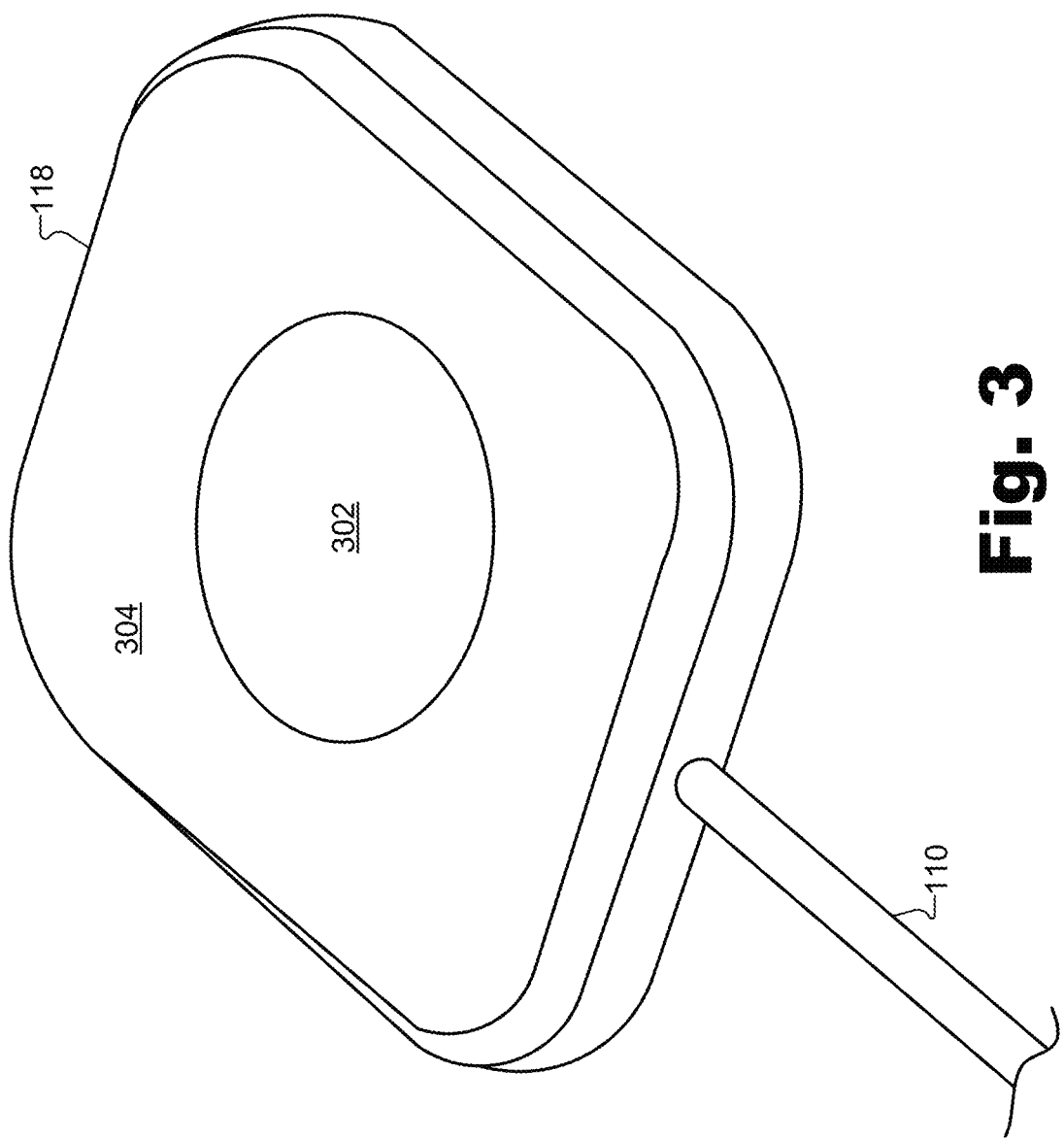
FIG. 3 illustrates a top perspective view of an exemplary implantable cochlear stimulator (ICS) casing according to principles described herein.

FIG. 3 illustrates an exemplary top perspective view of casing 118 of cochlear implant 108. As shown in FIG. 3, casing 118 is mechanically coupled to electrode lead 110 and includes, on a top surface thereof, a first surface area 302 and a second surface area 304. First surface area 302 corresponds to an area on casing 118 that is configured to serve as a current path to ground for electrical stimulation. In the example shown in FIG. 3, first surface area 302 has a circular shape. However, first surface area 302 may have any suitable shape (e.g., square, rectangular, etc.) as may serve a particular implementation. Second surface area 304 is indicated in FIG. 3 as a surface area on casing 118 that is adjacent to and that surrounds first surface area 302. However, second surface area 304 may correspond to any surface of casing 118 that is not configured to operate as a current path to ground (e.g., any surface of casing 118 other than first surface area 302).

Figure 4:
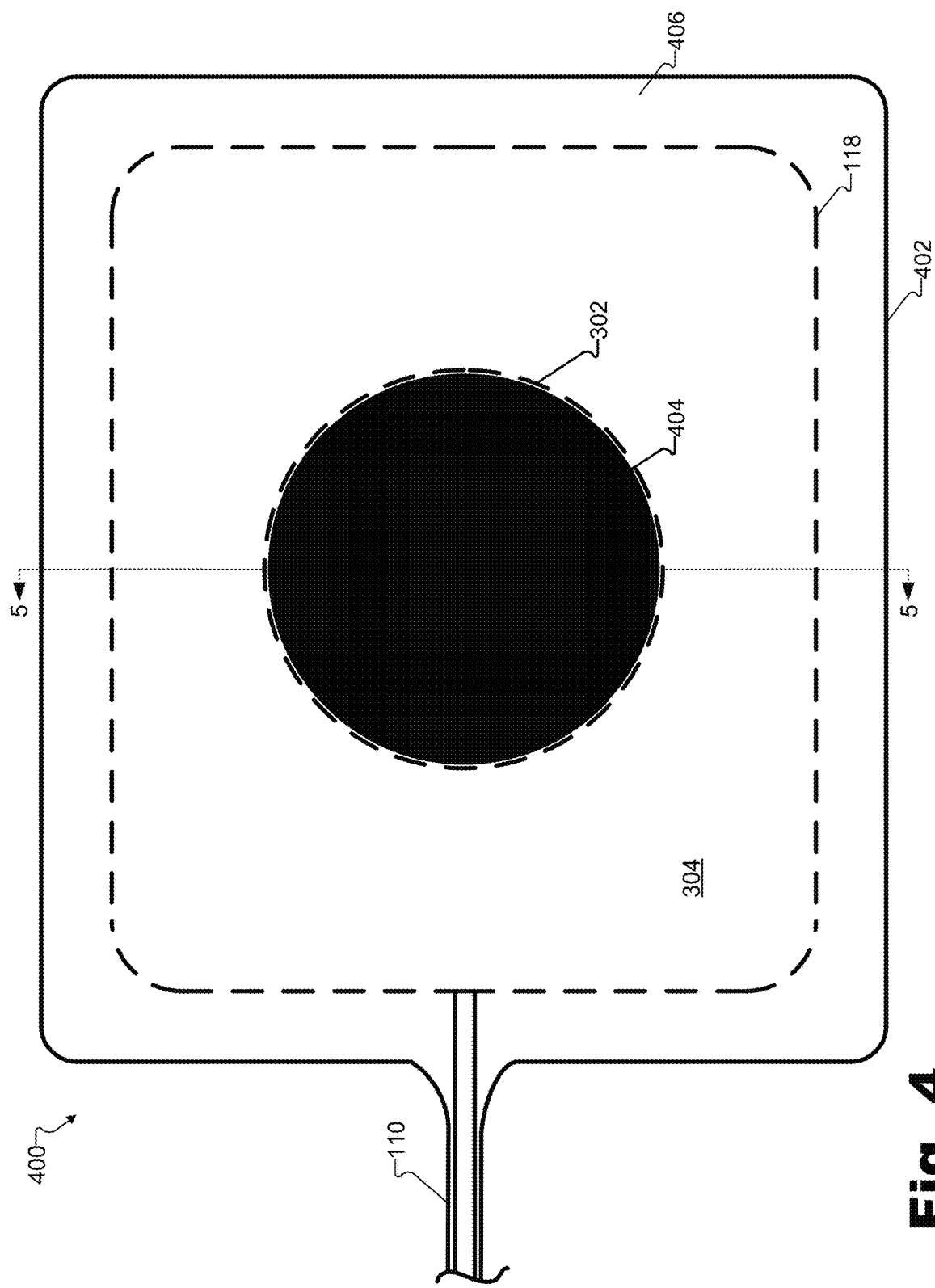
FIG. 4 illustrates a top plan view of an exemplary cochlear implant assembly that is configured to be implanted in a recipient according to principles described herein.

FIG. 4 illustrates a top plan view an exemplary cochlear implant assembly 400 that is configured to be implanted in a recipient. As shown in FIG. 4, cochlear implant assembly 400 includes casing 118 and an encapsulant 402. As shown, casing 118 is completely disposed within encapsulant 402, as is a portion of electrode lead 110. For illustrative purposes, casing 118 is represented by a dashed line in FIG. 4.

As shown, encapsulant 402 includes a conductive portion 404 and a non-conductive portion 406. In the example shown in FIG. 4, conductive portion 404 covers first surface area 302. With such a configuration, first surface area 302 and conductive portion 404 are in conductive contact with each other such that conductive portion 404 serves as the ground electrode for electrical stimulation provided by way of electrode lead 110. Non-conductive portion 406, on the other hand, covers the remaining surface areas of casing 118, including second surface area 304 of casing 118 shown in FIG. 4 that is not configured to serve as a current path to ground.

In the example shown in FIG. 4, conductive portion 404 has a circular shape so as to correspond to the same shape as first surface area 302. However, it is understood that conductive portion 404 may have any suitable shape (e.g., square, rectangular, etc.) as may serve a particular implementation, and does not necessarily have the same shape as first surface area 302.

In the example shown in FIG. 4, casing 118 is visible through non-conductive portion 406 of encapsulant because non-conductive portion 406 is formed of a transparent material such as medical grade silicone. In certain alternative examples, non-conductive portion 406 may be formed of a non-transparent material. Conductive portion 404 is illustrated as opaque in FIG. 4 due to, for example, conductive particles impregnated within conductive portion 404. However, conductive portion 404 may alternatively be transparent or translucent when made of inherently conductive transparent or translucent material that does not require the addition of conductive particles.

Figure 5:
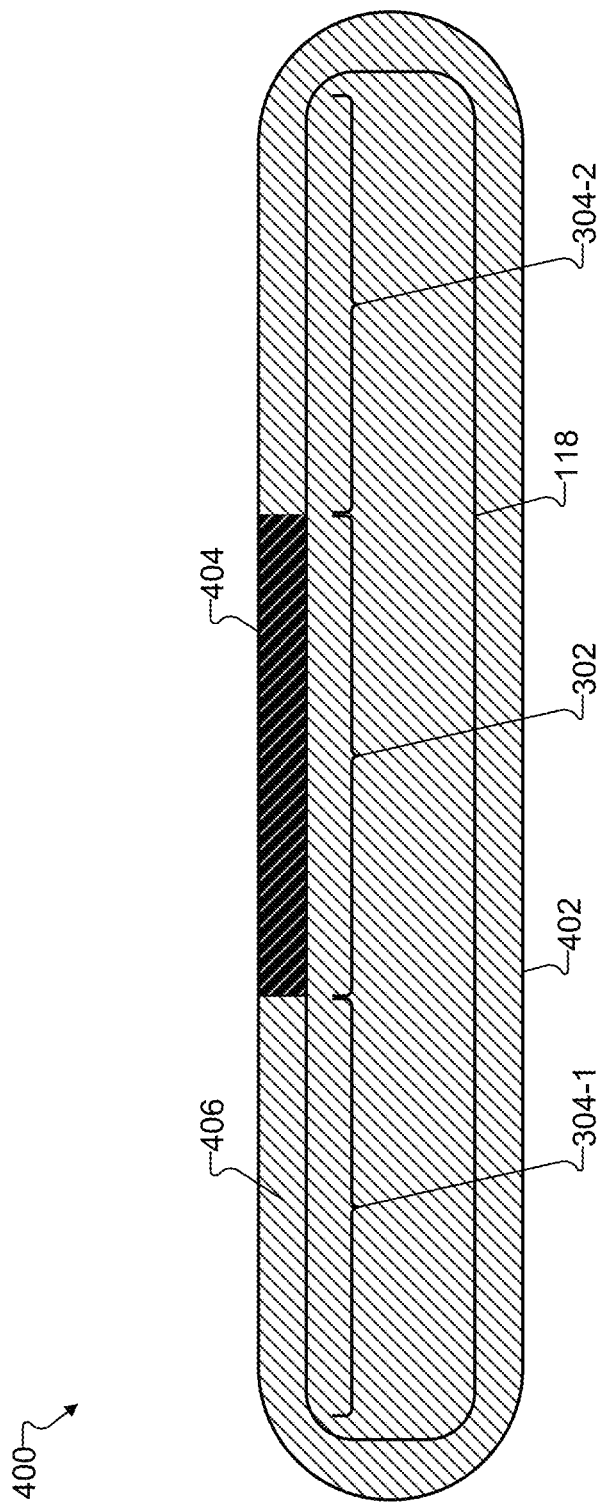
FIG. 5 is an exemplary cross section of the cochlear implant assembly shown in FIG. 4 that is taken along line 5 in FIG. 4 according to principles described herein.

FIG. 5 depicts a cross-sectional view of cochlear implant assembly 400 taken along line 5-5 in FIG. 4. The internal components (e.g., ICS 116) of cochlear implant 108 that are provided within casing 118 are omitted from FIG. 5 for simplicity. As shown in FIG. 5, conductive portion 404 of encapsulant 402 covers and is in conductive contact with first surface area 302 such that conductive portion 404 serves as the ground electrode. In certain examples, a layer of primer (not shown) may be provided on first surface area 302 between cochlear implant 108 and conductive portion 404. Such a primer may ensure that conductive portion 404 adheres to the material (e.g., titanium) that forms an outer casing 118 of cochlear implant 108. The primer may either be a conductive primer or may be provided in such a thin layer that the primer has a negligible insulating effect between the first surface area 302 and the conductive portion 404 serving as a ground electrode.

As shown in FIG. 5, non-conductive portion 406 of encapsulant 402 covers second surface areas 304-1 and 304-2 of casing 118. In a similar manner, a primer (not shown) may be applied to the surface (e.g., second surface areas 304-1 and 304-2) of casing 118 to ensure that non-conductive portion 406 adheres to casing 118. The primer applied, for example, to second surface areas 304-1 and 304-2 may be the same primer that is applied to first surface area 302 or may be a different primer depending on which material is used for conductive portion 404. Although second surface areas 304-1 and 304-2 are the only surfaces of casing 118 specifically identified in FIG. 5 as being non-conductive areas, it is understood that the entire surface area of casing 118 other than first surface area 302 may be considered as second surface area 304.

In the example shown in FIG. 5, conductive portion 404 is shown as being in direct contact with the outer casing 118. However, in certain alternative examples, a metal layer (not shown in FIG. 5) may be disposed between conductive portion 404 and casing 118 and configured to serve as a current path to ground. Such a metal layer may have any suitable shape when viewed in a plan view and any suitable thickness when viewed in a cross-sectional view as may serve a particular implementation. In addition, such a metal layer may include any suitable metal or combination of metals as may serve a particular implementation. For example, the metal layer may correspond to a platinum disc having a shape and size that matches first surface area 302. Such a metal layer may be attached to casing 118 in any suitable manner. For example, the metal layer may be welded to casing 118 or may be attached to casing 118 with a conductive adhesive. In examples where such a metal layer is provided between conductive portion 404 and casing 118, a primer may be applied to a surface the metal layer that faces away from casing 118 to facilitate conductive portion 404 adhering to the metal layer.

As shown in FIG. 5, conductive portion 404 and non-conductive portion 406 cover casing 118 such that casing 118 is entirely disposed within encapsulant 402. In addition, conductive portion 404 and non-conductive portion 406 together form a continuous coplanar exterior surface of encapsulant 402. With such a configuration, there is no void or opening in encapsulant 402 where the ground electrode is provided. As such, cochlear implant assembly 400 is less susceptible to biofilm formation at the ground electrode than conventional cochlear implant assemblies.

Figure 6:
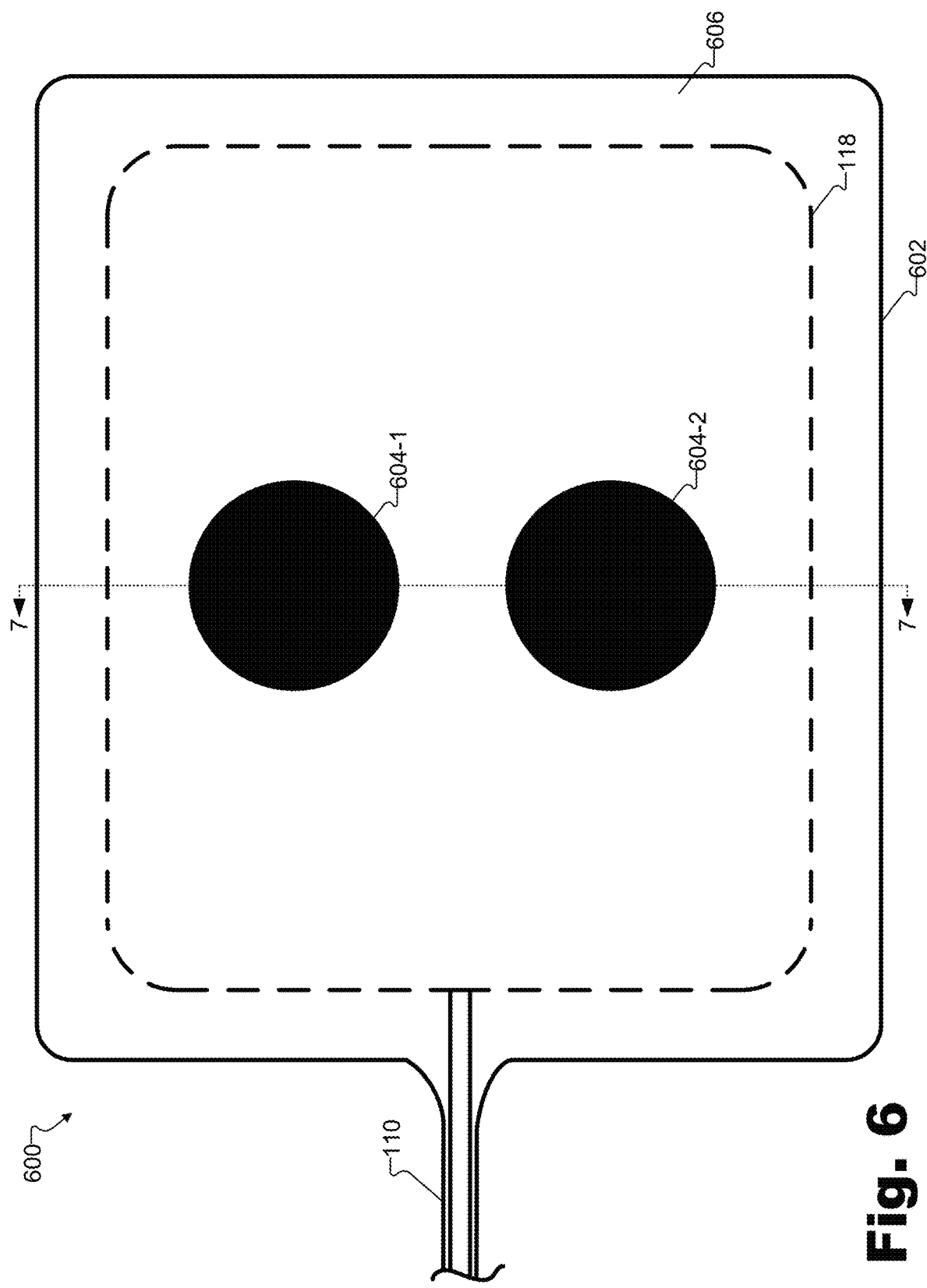
FIG. 6 illustrates another top plan view of an exemplary cochlear implant assembly that is configured to be implanted in a recipient according to principles described herein.

In certain alternative examples, an encapsulant may include a plurality of conductive portions that are conductively isolated one from another by the non-conductive portion of the encapsulant. To illustrate, FIG. 6 shows a top plan view of a cochlear implant assembly 600 in which an elastic encapsulant 602 includes a plurality of conductive portions 604 (e.g., conductive portions 604-1 and 604-2) and a non-conductive portion 606. Each conductive portion included in conductive portions 604 is configured to serve as a current path to ground for electrical stimulation. For illustrative purposes, casing 118 is represented by a dashed line in FIG. 4.

Although FIG. 6 only shows two conductive portions 604, it is understood that any suitable number of conductive portions 604 may be provided as may serve a particular implementation. In addition, in the example shown in FIG. 6, conductive portions 604-1 and 604-2 each have the same shape. However, it is understood that, in certain examples, conductive portions 604-1 and 604-2 may each have a different shape. For example, conductive portion 604-1 may have a circular shape and conductive portion 604-2 may have a square shape when viewed in a plan view.

Figure 7:
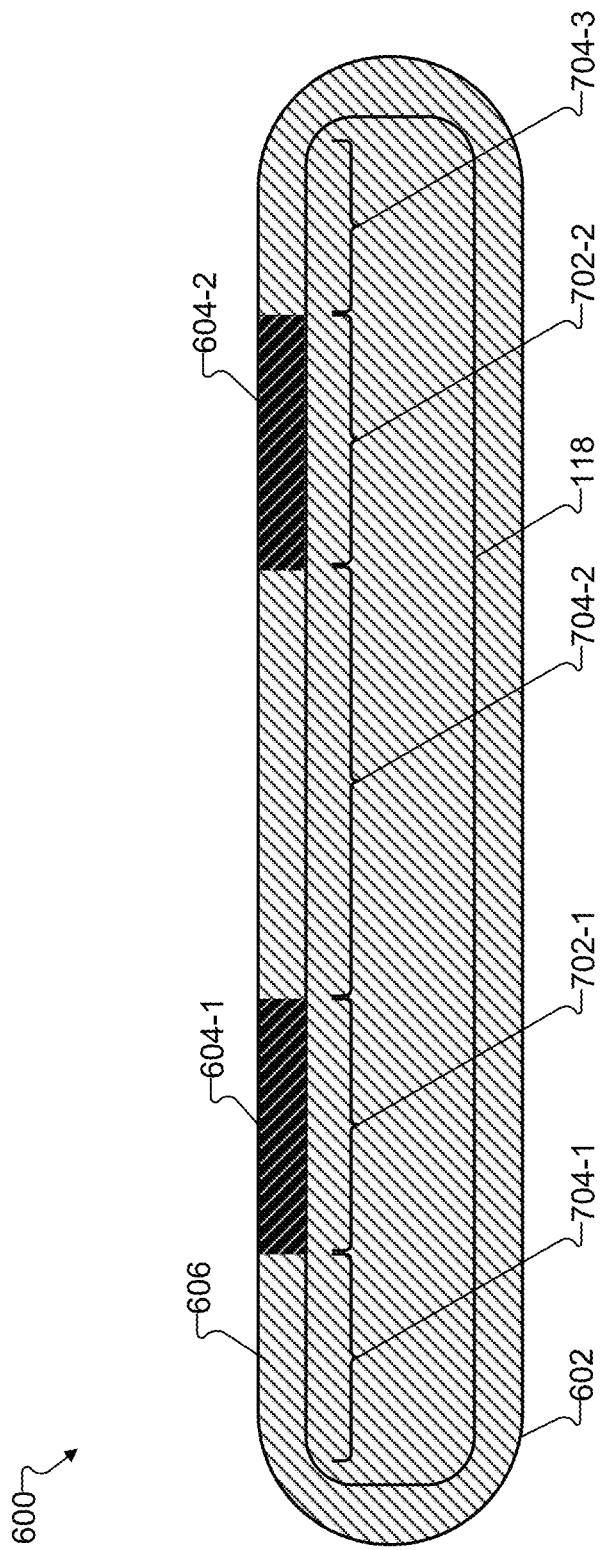
FIG. 7 is an exemplary cross section of the cochlear implant assembly shown in FIG. 6 that is taken along line 7 in FIG. 6 according to principles described herein.

FIG. 7 depicts a cross-sectional view of cochlear implant assembly 600 taken along line 7-7 in FIG. 6. The internal components (e.g., ICS 116) of cochlear implant 108 that are provided within casing 118 are omitted from FIG. 7 for simplicity. As shown in FIG. 7, cochlear implant 108 includes first surface areas 702 (e.g., first surface areas 702-1 and 702-2) and second surface areas 704 (e.g., second surface areas 704-1 through 704-3). As shown in FIG. 7, a non-conductive portion of encapsulant 602 is provided between conductive portion 604-1 and 604-2 such that conductive portion 604-1 is conductively isolated from conductive portion 604-2. Conductive portions 604 and non-conductive portions 606 together form a continuous coplanar exterior surface of encapsulant 602. With such a configuration, there is no void or opening in encapsulant 602 where the ground electrode is provided. As such, similar to cochlear implant assembly 400, cochlear implant assembly 600 also is less susceptible to biofilm formation at the ground electrode than conventional cochlear implant assemblies.

Figure 8:
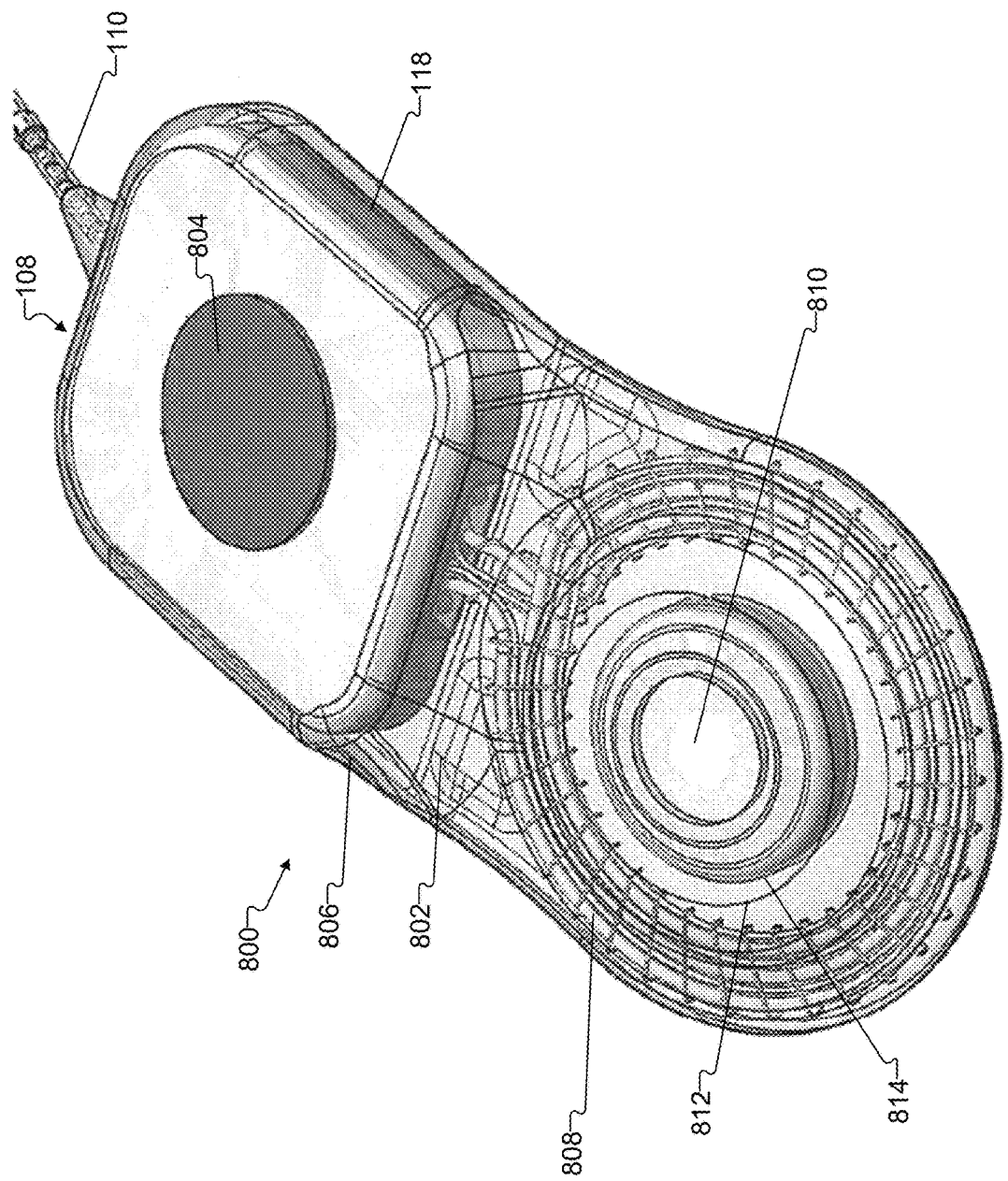
FIG. 8 illustrates a top perspective view of another exemplary cochlear implant assembly that is configured to be implanted in a recipient according to principles described herein.

In certain examples, a cochlear implant assembly may also include a cochlear implant antenna and a cochlear implant magnet or magnet apparatus that are each provided within an encapsulant. To illustrate, FIG. 8 depicts a perspective view of a cochlear implant assembly 800 that includes casing 118 housing ICS 116 of cochlear implant 108, an encapsulant 802 that includes a conductive portion 804 and a non-conductive portion 806, a cochlear implant antenna 808, and a cochlear implant magnet apparatus 810. Conductive portion 804 and non-conductive portion 806 shown in FIG. 8 are configured in a manner similar to conductive portion 404 and non-conductive portion 406 shown in FIG. 4.

Cochlear implant antenna 808 is configured to communicate with a headpiece antenna (not shown) that is included in a headpiece (e.g., headpiece 106) configured to be located external to the recipient. As shown in FIG. 8, cochlear implant antenna 808 is completely embedded within encapsulant 802.

Cochlear implant magnet apparatus 810 is configured to interact with a headpiece magnet (not shown) provided in a headpiece (e.g., headpiece 106) so as to maintain a position of the headpiece with respect to cochlear implant assembly 800. Any suitable material or combination of materials may be used for cochlear implant magnet apparatus 810 as may serve a particular implementation. For example, cochlear implant magnet apparatus 810 may correspond to a single permanent magnet, a ferromagnetic material, a ferrite magnet, a biocompatible magnet, a magnet apparatus comprising multiple magnets that is configured for safe use in magnetic resonance imaging (MRI), and/or any other suitable magnet as may serve a particular implementation. Examples of magnet apparatus configured for safe use in MRI are found in U.S. Pat. No. 9,919,154, which is assigned to the assignee of the present invention and hereby incorporated by reference in its entirety.

In the example shown in FIG. 8, cochlear implant magnet apparatus 810 is removably provided within a pocket 814 having a pocket opening 812 formed in encapsulant 802. Pocket 814 may have any suitable size and/or shape to sufficiently retain cochlear implant magnet apparatus 810 within pocket 814 but allow cochlear implant magnet apparatus 810 to be removed, if needed. With such a configuration, it is possible to remove cochlear implant magnet apparatus 810 if the recipient has to undergo, for example, an MRI procedure that may cause cochlear implant magnet apparatus 810 to dislodge from pocket 814, flip, or otherwise cause damage to the cochlear implant assembly or the recipient, or that requires magnet apparatus removal to avoid artifact in the MRI image.

In certain alternative examples, an encapsulant may include a pocket in which the magnet apparatus resides, but not include a pocket opening. In such examples, the cochlear implant assembly may include an MRI compliant magnet apparatus that does not require removal in most cases if the recipient has to undergo an MRI procedure, but that could be removed as necessary in some cases by making an incision in the encapsulant to access the magnet pocket and remove the magnet apparatus. One or more techniques and/or tools taught in U.S. patent application Ser. No. 16/101,390 entitled, "Magnet Removal and Replacement Apparatus and Methods for Use with Cochlear Implants," assigned to the assignee of the present invention, and hereby incorporated by reference in its entirety, could be used. With such a cochlear implant configuration, it is possible to prevent biofilm formation not only in a region around the ground electrode but also in a region of the encapsulant (e.g., encapsulant 802) that includes the cochlear implant magnet apparatus (e.g., cochlear implant magnet apparatus 810), while still allowing magnet apparatus removal in the rare case that removal is needed.

In yet another alternative example, an encapsulant may not include a pocket in which a cochlear implant magnet apparatus is removably inserted. Instead, the cochlear implant magnet apparatus may be completely embedded within the encapsulant such that there is no opening or void in the encapsulant where the cochlear implant magnet apparatus is located. In such examples, the cochlear implant assembly may include an MRI compliant magnet apparatus that does not have to be removed if the recipient has to undergo, for example, an MRI procedure. With such a configuration, it is possible to prevent biofilm formation not only in a region around the ground electrode but also in a region of the encapsulant (e.g., encapsulant 802) that includes the cochlear implant magnet apparatus (e.g., cochlear implant magnet apparatus 810).

Figure 9:
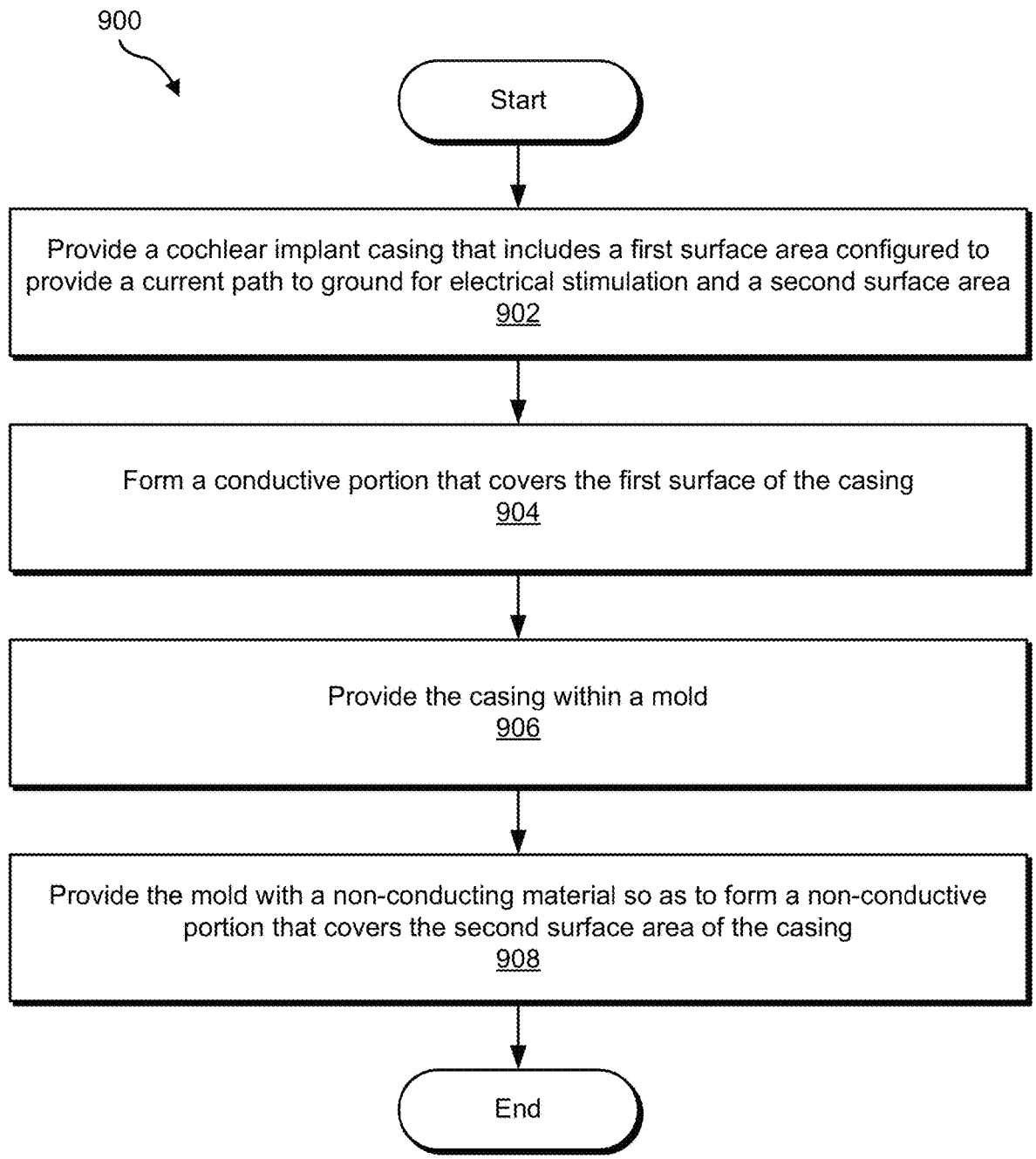
FIG. 9 shows an exemplary method for manufacturing a cochlear implant assembly according to principles described herein.

FIG. 9 illustrates a method 900 for manufacturing a cochlear implant assembly (e.g., cochlear implant assembly 400). While FIG. 9 illustrates exemplary operations according to one embodiment, other embodiments may omit, add to, reorder, and/or modify any of the operations shown in FIG. 9.

In operation 902, an ICS (e.g., ICS 116) housed within a casing (e.g., casing 118) is provided. As described herein, the casing 118 includes a first surface area configured to provide a current path to ground for electrical stimulation and a second surface area. Operation 902 may be performed in any of the ways described herein.

In operation 904, conductive material is applied on the first surface area of the casing so as to form a conductive portion that covers the first surface area. The conductive material may be applied to the first surface area in any suitable manner and at any suitable time. In certain examples, a primer may be applied to the first surface area of the casing prior to applying the conductive elastic material to the first surface area. In addition, the conductive material may be cured using any suitable curing process (e.g., heat curing) after the conductive material is applied to the first surface area. Operation 904 may be performed in any of the ways described herein.

In operation 906, the casing is inserted within a mold. Operation 906 may be performed in any of the ways described herein.

In operation 908, the mold is provided with a non-conducting material (e.g., silicone) so as to form a non-conductive portion that covers a second surface area of the casing. The mold may be provided with the non-conducting material in any suitable manner. In certain examples, the non-conducting material may be injected into the mold such that such that the non-conductive portion is formed when the non-conducting material solidifies. Alternatively, the non-conducting material may be compression molded in the mold (e.g., by providing the non-conducting material in a first half of the mold and then pressing a second half of the mold onto the non-conducting material provided in the first half of the mold). Operation 908 may be performed in any of the ways described herein.

In certain examples, operation 904 may be performed prior to operations 906 and 908. In such examples, operation 904 may include providing the conductive material within an additional mold that defines a shape (e.g., a circular shape, a square shape, etc.) of the conductive portion. For example, the additional mold may be provided on a surface of a casing (e.g., casing 118. The conductive material may then be provided within the additional mold. The conductive material may then be subjected to a curing process such that, when the additional mold is removed, the conductive portion protrudes as a layer of conductive material from the surface of the casing. The casing with the protruding conductive portion disposed thereon may then be provided within the mold that defines the shape of the non-conductive portion such that the non-conductive elastic material fills in around the conductive portion and together form the encapsulant.

In certain alternative examples, operation 904 may be performed after operations 906 and 908. In such examples, the cochlear implant is provided within the mold, and the non-conductive portion is formed such that the non-conductive portion substantially covers each surface area of the casing of the cochlear implant other than the surface area configured to provide a current path to ground, and leaves exposed at least a substantial portion of the surface area of the casing of the cochlear implant that is configured to provide a current path to ground. This exposed portion is recessed compared to the surface of the non-conductive portion, and this void may then be filled in with conductive material in any suitable manner such that there is no longer a void and the conductive portion and the non-conductive portion form the encapsulant that entirely covers the casing of the cochlear implant. In certain examples, the conductive portion may be cured such that the conductive material bonds to the edges of the non-conductive material and to the surface configured to provide a current path to ground.

In certain examples, the methods of manufacturing a cochlear implant assembly described herein may also include communicatively coupling a cochlear implant antenna to the cochlear implant and providing the cochlear implant antenna within the mold. In such examples, the non-conducting material is provided in the mold such that the cochlear implant antenna is completely embedded within the non-conducting elastic material together with the casing housing the ICS.

In certain examples, the mold that defines the shape of the non-conducting portion of the encapsulant may include a portion that defines a pocket into which a cochlear implant magnet apparatus is removably insertable. In such examples, the cochlear implant magnet apparatus may be inserted within the pocket after the elastic encapsulant is formed.

In certain alternative examples, the cochlear implant magnet apparatus may be inserted within the mold together with the cochlear implant antenna and the cochlear implant such that the cochlear implant antenna, the cochlear implant, and the cochlear implant magnet apparatus are all completely embedded within the encapsulant when the non-conducting material solidifies. The cochlear implant magnet apparatus may not be removable from the encapsulant without cutting into the encapsulant to expose the cochlear implant magnet apparatus.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant assembly adapted for insertion into a recipient, comprising:
    an implantable cochlear stimulator (ICS) configured to apply electrical stimulation to the recipient by way of an electrode array;
    a casing that houses the ICS and that comprises a first surface area configured to serve as a current path to ground for the electrical stimulation and a second surface area; and
    an encapsulant that includes
        a conductive portion configured to cover the first surface area of the casing and be in conductive contact with the first surface area such that the conductive portion serves as the ground electrode, and
        a non-conductive portion configured to cover the second surface area of the casing such that the casing is entirely disposed within the conductive and non-conductive portions of the encapsulant,
    wherein the conductive portion and the non-conductive portion form a continuous coplanar exterior surface of the encapsulant.

2. The cochlear implant assembly of claim 1, wherein the conductive portion of the encapsulant includes a plurality of conductive portions conductively isolated one from another by the non-conductive portion of the encapsulant.

3. The cochlear implant assembly of claim 1, wherein the conductive portion of the encapsulant is formed of silicone that is impregnated with conductive particles.

4. The cochlear implant assembly of claim 1, wherein the first surface area of the casing faces away from a skull of the recipient when the cochlear implant assembly is inserted into the recipient.

5. The cochlear implant assembly of claim 1, further comprising:
    a cochlear implant antenna embedded within the encapsulant and communicatively coupled to the ICS; and
    a cochlear implant magnet apparatus embedded within the encapsulant,
    wherein
        the cochlear implant antenna is configured to communicate with a headpiece antenna that is included in a headpiece configured to be located external to the recipient, and
        the cochlear implant magnet apparatus is configured to interact with a headpiece magnet provided in the headpiece so as to maintain a position of the headpiece with respect to the cochlear implant assembly.

6. The cochlear implant assembly of claim 5, wherein the cochlear implant magnet apparatus is removably inserted within a pocket formed in the encapsulant.

7. The cochlear implant assembly of claim 5, wherein:
    the cochlear implant magnet apparatus is configured for safe use during magnetic resonance imaging (MRI); and
    the encapsulant covers the cochlear implant magnet apparatus such that the cochlear implant magnet apparatus is completely embedded within the encapsulant and is not removable from the encapsulant.

8. A cochlear implant assembly adapted for insertion into a recipient, comprising:
    an implantable cochlear stimulator (ICS) configured to apply electrical stimulation to the recipient by way of an electrode array;
    a casing that houses the ICS and that comprises a first surface area configured to provide a current path to ground for the electrical stimulation and a second surface area;
    an encapsulant that includes
        a conductive portion configured to cover the first surface area of the casing and be in conductive contact with the first surface area such that the conductive portion serves as the ground electrode, and
        a non-conductive portion configured to cover the second surface area of the casing such that the casing is entirely disposed within the conductive and non-conductive portions of the encapsulant; and a magnet apparatus that is configured to be safely used during magnetic resonance imaging (MRI) and is embedded within the encapsulant, the MRI compliant magnet apparatus configured to interact with a headpiece magnet apparatus included in a headpiece configured to be located external to the recipient so as to maintain a position of the headpiece with respect to the cochlear implant assembly, wherein the conductive portion and the non-conductive portion form a continuous coplanar exterior surface of the encapsulant.

9. The cochlear implant assembly of claim 8, wherein the encapsulant covers the magnet apparatus such that the magnet apparatus is completely embedded within the encapsulant and is not removable from the encapsulant.

10. The cochlear implant assembly of claim 8, wherein the conductive portion of the encapsulant is formed of silicone that is impregnated with conductive particles.

11. The cochlear implant assembly of claim 8, wherein the first surface area of the cochlear implant faces away from a skull of the recipient when the cochlear implant assembly is inserted into the recipient.

12. A method of manufacturing a cochlear implant assembly adapted for insertion into a recipient, the method comprising:
providing an implantable cochlear stimulator (ICS) configured to apply electrical stimulation to the recipient by way of an electrode array, the ICS housed within a casing including a first surface area configured to provide a current path to ground for the electrical stimulation and a second surface area;
applying a conductive material on the first surface area of the casing so as to form a conductive portion that covers the first surface area of the casing and that is in conductive contact with the first surface area such that the conductive portion serves as the ground electrode;
providing the casing within a mold; and
providing the mold with a non-conducting material so as to form a non-conductive portion that covers the second surface area of the casing,
wherein
the conductive portion and the non-conductive portion together form an encapsulant that completely covers the casing, and
the conductive portion and the non-conductive portion form a continuous coplanar exterior surface of the encapsulant.

13. The method of claim 12, wherein the applying of the conductive material on the first surface area of the casing includes providing the conductive material within an additional mold that defines a shape of the conductive portion.

14. The method of claim 13, wherein the providing of the casing within the mold includes providing the casing and the conductive portion disposed thereon into the mold.

15. The method of claim 12, further comprising:
applying primer to the first surface area of the casing prior to the applying of the conductive material on the first surface area of the casing; and
curing the conductive material after the applying of the conductive material on the first surface area of the casing.

16. The method of claim 12, wherein the forming of the conductive portion is performed after the forming of the non-conductive portion.

17. The method of claim 16, wherein the applying of the conductive material on the first surface area of the casing comprises providing the conductive material in a void formed in the non-conductive portion that exposes the first surface area of the casing.

18. The method of claim 12, further comprising:
communicatively coupling a cochlear implant antenna to the cochlear implant;
providing the cochlear implant antenna within the mold; and
providing a cochlear implant magnet apparatus within the mold;
wherein
the providing of the mold with the non-conducting elastic material includes embedding the cochlear implant antenna and the cochlear implant magnet apparatus within the non-conducting elastic material,
the cochlear implant antenna is configured to communicate with a headpiece antenna that is included in a headpiece configured to be located external to the recipient, and
the cochlear implant magnet apparatus is configured to interact with a headpiece magnet provided in the headpiece so as to maintain a position of the headpiece with respect to the cochlear implant assembly.

19. The method of claim 18, wherein:
the cochlear implant magnet apparatus is configured to be safely used during a magnetic resonance imaging (MRI); and
the encapsulant covers the cochlear implant magnet apparatus such that the cochlear implant magnet apparatus is completely embedded within the encapsulant and is not removable from the encapsulant.

20. The method of claim 12, wherein the conductive portion of the encapsulant is formed of silicone that is impregnated with conductive particles.

* * * * *